United States Patent [19]

Yamamoto et al.

[11] Patent Number: 6,160,171

[45] Date of Patent: Dec. 12, 2000

[54] TRIFLUORO-SUBSTITUTED BENZOIC ACID, ESTERS THEREOF, AND PROCESS FOR PRODUCING THE SAME

[75] Inventors: Yasuhito Yamamoto; Yasuhiro Yoneda; Kikuo Ataka; Naoyuki Yokota, all of Ube, Japan

[73] Assignee: Ube Industries, Ltd., Yamaguchi, Japan

[21] Appl. No.: 09/242,441

[22] PCT Filed: Aug. 19, 1997

[86] PCT No.: PCT/JP97/02856

§ 371 Date: Feb. 17, 1999

§ 102(e) Date: Feb. 17, 1999

[87] PCT Pub. No.: WO98/07682

PCT Pub. Date: Feb. 26, 1998

[30] Foreign Application Priority Data

Aug. 19, 1996 [JP] Japan .................................. 8-217045
Aug. 19, 1996 [JP] Japan .................................. 8-217046

[51] Int. Cl.[7] .................................................. C07C 51/363

[52] U.S. Cl. .............................................. 562/494; 560/103
[58] Field of Search ............................. 560/103; 562/494

[56] References Cited

FOREIGN PATENT DOCUMENTS 4301245   7/1994   Germany .
9-67303   3/1997   Japan .

*Primary Examiner*—Cecilia Tsang
*Assistant Examiner*—Taofiq A. Solola
*Attorney, Agent, or Firm*—Jordan and Hamburg LLP

[57] ABSTRACT

The present invention is to provide a trifluoro-substituted benzoic acid, an ester thereof, particularly 2,3,4-trifluoro-5-iodobenzoic acid, 2,3,4-trifluoro-5-trifluoromethylbenzoic acid, esters thereof, which are useful as a starting material for synthesizing a quinolonecarboxylic acid compound useful as a medicine, an anti-bacterial agent or an antiviral agent, and processes for preparing these compounds and 2,4,5-trifluoro-3-iodobenzoic acid, 2,4,5-trifluoro-3-trifluoromethylbenzoic acid and esters thereof.

7 Claims, No Drawings

TRIFLUORO-SUBSTITUTED BENZOIC ACID, ESTERS THEREOF, AND PROCESS FOR PRODUCING THE SAME

This application is a 371 of PCT/JP97/02856 filed Aug. 19, 1997.

TECHNICAL FIELD

This invention relates to a trifluoro-substituted benzoic acid, esters thereof and the processes for preparing the same, more specifically, to a 2,3,4-trifluoro-5-substituted benzoic acid, esters thereof and the novel processes for preparing the same and 2,4,5-trifluoro-3-substituted benzoic acid esters.

BACKGROUND ART

The above-mentioned trifluoro-substituted benzoic acid and esters thereof are useful as a starting material for preparing 2,3,4-trifluoro-5-trifluoromethylbenzoic acid or 2,4,5-trifluoro-3-trifluoromethylbenzoic acid which is an important intermediate for synthesis of quinolone carboxylic acids useful as, for example, a medicine, particularly as an anti-bacterial or antiviral agent. Trifluoro-trifluoromethylbenzoic acids can be converted into quinolone carboxylic acids having a 6- or 8-trifluoromethyl group according to the method as disclosed in, for example, WO 96/02512 publication or Japanese Provisional Patent Publication No. 66180/1989.

As methods for preparing 2,4,5-trifluoro-3-iodobenzoic acid derivatives which are starting materials for producing 2,4,5-trifluoro-3-trifluoromethylbenzoic acid, it has been known the method for preparing 2,4,5-trifluoro-3-iodobenzoic acid from 3-amino-2,4,5-trifluorobenzoic acid by the Sandmeyer's reaction. More specifically, the methods shown below may be mentioned.

(1) In Japanese Provisional Patent Publication No. 95176/1991, there is disclosed a method for obtaining 2,4,5-trifluoro-3-iodobenzoic acid by reacting cuprous iodide, tert-butyl nitrite and 3-amino-2,4,5-trifluorobenzoic acid in acetonitrile.

(2) In Japanese Provisional Patent Publication No. 88157/1988 and Japanese Provisional Patent Publication No. 25125/1994, there are disclosed a method for obtaining 2,4-dichloro-5-fluoro-3-iodobenzoic acid by reacting 3-amino-2,4-dichloro-5-fluorobenzoic acid with hydrochloric acid and sodium nitrite to once form a diazonium salt, and then, reacting it with potassium iodide.

However, in the above-mentioned method (1), many side reactions proceed and the yield is 50% or less, and thus, it is not an industrially satisfied method. Also, the above-mentioned method (2) is not an industrially satisfied method in the point that the yield is less than 60%.

Accordingly, neither of the known method (1) or (2) is satisfactory as a method for obtaining 2,4,5-trifluoro-3-iodobenzoic acid.

Also, in Japanese Provisional Patent Publication No. 66180/1989 and WO 96/02512 publication, there is disclosed a method for preparing 2,4,5-trifluoro-3-trifluoromethyl-benzoic acid by lithiating 1-bromo-2,4,5-trifluoro-3-trifluoromethylbenzene with n-butyl lithium, etc., and incorporating the carboxyl group by carbon dioxide.

However, the above-mentioned method has the following disadvantageous points. That is, (1) It has been reported that lithium compounds having a trifluoromethyl group at the benzene ring, such as m-trifluoromethylphenyl lithium even without fluorine substituent has an explosive property, and still more polyfluorophenyl lithium also has an explosive property (see Chemistry and Industry, p. 1017 (1971), Chem. Eng. News, 1961, vol. 39, No. 16, p. 43).

(2) It has been reported that a trifluoromethylphenyl magnesium compound obtained from a trifluoromethylhalobenzene by the Grignard reaction shows the similar reactivity as that of the above-mentioned lithium compound and a carboxyl group can be introduced by carbon dioxide, but the compound also has an explosive property. (see Chemistry and Industry, p. 120 (1971)).

Accordingly, it can be expected as a matter of course that 2,4,5-trifluoro-3-trifluoromethylphenyl lithium which is obtained by lithiating 1-bromo-2,4,5-trifluoro-3-trifluoromethylbenzene also has an explosive property. In the conventionally known methods, it is expected to cause an explosion during the process which is a significant problem in industrial production, so that it is not quite satisfactory as a method for producing 2,4,5-trifluoro-3-trifluoromethylbenzoic acid esters.

Also, the method for producing an aromatic trifluoromethyl compound by reacting an aromatic iodine compound with 2,2-difluoro-(fluorosulfonyl)acetic acid ester in the presence of a copper catalyst has been known (see the following literature).

However, there is no report about a compound having an ester group as an aromatic substituent. As a reaction mechanism of this reaction, it has been proposed that the ester group of the 2,2-difluoro-(fluorosulfonyl)acetic acid ester initially reacts with the copper catalyst. (For example, see J. Chem. Soc., Chem. Commun., 1989, p. 705, J. Chem. Soc., Perkin Trans. I, 1989, p.2385, J. Fluorine Chem., 45 (1989) p. 435, J. Fluorine Chem., 66 (1994) p.167, J. Fluorine Chem., 72 (1995) p. 241).

Thus, when a compound having an ester group as the aromatic substituent is applied to the present reaction, it is expected that the aromatic ester substituent reacts with the copper catalyst and that the desired compound cannot be obtained. In the reaction of chloroformic acid ethyl ester which is an aliphatic ester, an yield of trifluoromethylation is extremely low, as low as 5% (see Tetrahedron Letters, 32 (1991) p. 7689).

The present inventors have earnestly studied the cause of the low yield by the method disclosed in Japanese Provisional Patent Publication No. 95176/1991 for the purpose of producing 2,4,5-trifluoro-3-iodobenzoic acid. The present inventors have investigated the reaction conditions of the above-mentioned Sandmeyer's reaction to overcome the low yield but the yield did not improve under any of these conditions. As a result of the intensive investigations into the causes, they have judged that there is a limit to improve the yield by the method of using a usual iodine source or the method of reacting with an iodine source after the formation of the diazonium salt since a diazonium salt of 2,4,5-trifluorobenzoic acid which is formed during the reaction is extremely unstable, whereby they have earnestly investigated into the iodine source and the reaction method.

As a result, they have found that by using hydriodic acid as an acid and iodine sources, and adding an alkali metal nitrite to a mixed heterogeneous solution of hydriodic acid, a cuprous halide and 3-amino-2,4,5-trifluorobenzoic acid, an iodizing reaction proceeds simultaneously with the formation and decomposition of an unstable diazonium salt whereby a side reaction can be controlled and the yield can be improved. Thus, they have accomplished the present invention. According to the present invention, the yield which had never conventionally exceeded 60% is markedly improved and the yield of nearly 90% can be accomplished.

The present inventors have also earnestly investigated to overcome the problems involved in the above-mentioned conventionally known process for producing 2,4,5-trifluoro-3-trifluoromethylbenzoic acid. As a result, when an ester of the above-mentioned 2,4,5-trifluoro-3-iodobenzoic acid and a 2,2-difluoro-(fluorosulfonyl)acetic acid ester are reacted in the presence of a copper catalyst in an organic solvent, a 2,4,5-trifluoro-3-trifluoromethylbenzoic acid ester can be obtained with a good yield without no explosive property as mentioned above to accomplish the present invention.

On the other hand, 2,3,4-trifluoro-5-trifluoromethylbenzoic acid and an ester thereof, and 2,3,4-trifluoro-5-iodobenzoic acid and an ester thereof which are starting materials of the present invention are compounds not yet described in any literature.

The present inventors have found that, for the purpose of producing 2,3,4-trifluoro-5-trifluoromethylbenzoic acid as a starting material for synthesizing a novel quinolonecarboxylic acid series compound having a trifluoromethyl group at the 6-position, when a 2,3,4-trifluoro-5-iodobenzoic acid ester and a 2,2-difluoro-(fluorosulfonyl) acetic acid ester are reacted in the presence of a copper catalyst in an organic solvent, a novel 2,3,4-trifluoro-5-trifluoromethylbenzoic acid ester can be obtained with a good yield whereby they have accomplished the present invention.

The present inventors have further continued earnest studies to obtain 2,3,4-trifluoro-5-iodobenzoic acid which is a starting material for producing 2,3,4-trifluoro-5-trifluoromethylbenzoic acid. As a result, they have found that, by using hydriodic acid as an iodine source, and adding an alkali metal nitrite to a mixed heterogeneous solution of hydriodic acid, a cuprous halide and 5-amino-2,3,4-trifluorobenzoic acid, an iodizing reaction proceeds simultaneously with formation and decomposition of an unstable diazonium salt and the desired 2,3,4-trifluoro-5-iodobenzoic acid can be obtained while controlling a side reaction with a high yield, and consequently they, have accomplished the present invention. The obtained 2,3,4-trifluoro-5-iodobenzoic acid can be converted into a 2,3,4-trifluoro-5-iodobenzoic acid ester by the usual esterifying method with a high yield.

Accordingly, the first object of the present invention is to provide 2,3,4-trifluoro-5-(trifluoromethyl or iodo)-benzoic acid and an ester thereof.

The second object of the present invention is to provide a process for producing a 2,3,4-trifluoro-5-trifluoromethylbenzoic acid ester by allowing a 2,3,4-trifluoro-5-iodobenzoic acid ester to react with a 2,2-difluoro-(fluorosulfonyl)acetic acid ester in the presence of a copper catalyst in an organic solvent.

The third object of the present invention is to provide a process for producing 2,4,5-trifluoro-3-iodobenzoic acid with a good yield by allowing 3-amino-2,4,5-trifluorobenzoic acid to react with hydriodic acid in the presence of an alkali metal nitrite and a cuprous halide.

The fourth object of the present invention is to provide a process for producing a 2,4,5-trifluoro-3-trifluoromethylbenzoic acid ester with a good yield by allowing a 2,4,5-trifluoro-3-iodobenzoic acid ester to react with a 2,2-difluoro-(fluorosulfonyl)acetic acid ester in the presence of a copper catalyst in an organic solvent.

The fifth object of the present invention is to provide 2,3,4-trifluoro-5-iodobenzoic acid and an ester thereof, and a process for producing 2,3,4-trifluoro-5-iodobenzoic acid with a good yield by allowing 5-amino-2,3,4-trifluorobenzoic acid to react with hydriodic acid in the presence of an alkali metal nitrite and a cuprous halide.

DISCLOSURE OF THE INVENTION

The present invention relates to (1) a 2,3,4-trifluoro-5-substituted benzoic acid and an ester thereof represented by the formula (I):

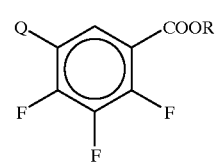

(I)

wherein R represents a hydrogen atom, a $C_1$ to $C_{10}$ alkyl group, a $C_3$ to $C_{10}$ cycloalkyl group or a $C_7$ to $C_{10}$ aralkyl group; and Q represents a trifluoromethyl group or an iodine atom, (2) a process for preparing a trifluoro-trifluoromethylbenzoic acid ester represented by the formula (II):

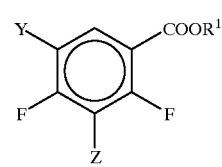

(II)

wherein $R^1$ represents a $C_1$ to $C_{10}$ alkyl group, a $C_3$ to $C_{10}$ cycloalkyl group or a $C_7$ to $C_{10}$ aralkyl group; Y represents a trifluoromethyl group or a fluorine atom; Z represents a fluorine atom when Y is a trifluoromethyl group, or a trifluoromethyl group when Y is a fluorine atom, which comprises allowing a trifluoro-iodobenzoic acid eater represented by the formula (III):

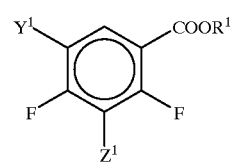

(III)

wherein $R^1$ has the same meaning as defined above; $Y^1$ represents a fluorine atom or an iodine atom; $Z^1$ represents an iodine atom when $Y^1$ is a fluorine atom, or a fluorine atom when $Y^1$ is an iodine atom, to react with a 2,2-difluoro-(fluorosulfonyl)acetic acid ester represented by the formula (IV):

$FO_2SCF_2COOR^1$ (IV)

wherein $R^1$ has the same meaning as defined above, in the presence of a copper catalyst in an organic solvent, and (3) a process for producing trifluoro-iodobenzoic acid represented by the formula (III'):

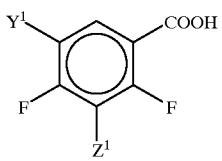

(III')

wherein $Y^1$ represents a fluorine atom or an iodine atom; $Z^1$ represents an iodine atom when $Y^1$ is a fluorine atom, or a fluorine atom when $Y^1$ is an iodine atom, which comprises allowing an amino-trifluorobenzoic acid represented by the formula (V):

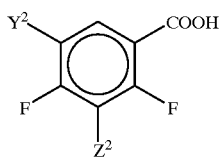

(V)

wherein $Y^2$ represents an amino group or a fluorine atom; $Z^2$ represents a fluorine atom when $Y^2$ is an amino group, or an amino group when $Y^2$ is a fluorine atom, to react with hydriodic acid in the presence of an alkali metal nitrite and a cuprous halide represented by the formula (VI):

CuX  (VI)

wherein X represents a halogen atom, in a solvent.

Best Mode for Practicing the Invention

The desired embodiments of the present invention are as follows.

(i) The compound described in the above (1) wherein the compound represented by the formula (I) (hereinafter also referred to as Compound (I)) is 2,3,4-trifluoro-5-iodobenzoic acid, ethyl 2,3,4-trifluoro-5-iodobenzoate, 2,3,4-trifluoro-5-trifluoromethylbenzoic acid, or ethyl 2,3,4-trifluoro-5-trifluoromethylbenzoate.

(ii) The producing process of the compound as described in the above (2) wherein the organic solvent is dimethylformamide or dimethylacetamide.

(iii) The producing process of the compound as described in the above (2) wherein the copper catalyst is cuprous iodide.

(iv) The producing process of the compound as described in the above (2) wherein R of the 2,3,4-trifluoro-5-iodobenzoic acid ester or the 2,4,5-trifluoro-3-iodobenzoic acid ester is an alkyl group having 1 to 4 carbon atoms.

(v) The producing process of the compound as described in the above (2) wherein the 2,2-difluoro-(fluorosulfonyl)acetic acid ester is an alkyl ester having 1 to 4 carbon atoms of 2,2-difluoro-(fluorosulfonyl) acetic acid.

(vi) The producing process of the compound as described in the above (3) wherein an alkali metal nitrite is added to a mixed heterogeneous solution of 5-amino-2,3,4-trifluorobenzoic acid or 3-amino-2,4,5-trifluorobenzoic acid, hydriodic acid and cuprous halide.

(vii) The process as described in the above (3) wherein the cuprous halide is cuprous iodide.

(viii) The process as described in the above (3) wherein an amount of the cuprous halide to be used is a stoichiometric amount or less based on the amount of 5-amino-2,3,4-trifluorobenzoic acid or 3-amino-2,4,5-trifluorobenzoic acid.

(ix) The process as described in the above (3) wherein an amount of hydriodic acid to be used is 2.5 to 10 moles per mole of 5-amino-2,3,4-trifluorobenzoic acid or 3-amino-2,4,5-trifluorobenzoic acid.

(x) The process as described in the above (3) wherein the alkali metal nitrite is sodium nitrite or potassium nitrite.

In the compound of the present invention, R in the compound (I) represented by the formula (I) represents a hydrogen atom, a $C_1$ to $C_{10}$ alkyl group, a $C_3$ to $C_{10}$ cycloalkyl group or a $C_7$ to $C_{10}$ aralkyl group.

As the $C_1$ to $C_{10}$ alkyl group represented by R of the compound (I), there may be mentioned, for example, a straight or branched alkyl group having 1 to 10 carbon atoms such as a methyl group, an ethyl group, a propyl group (including respective isomers), a butyl group (including respective isomers), a pentyl group (including respective isomers), a hexyl group (including respective isomers), a heptyl group (including respective isomers), an octyl group (including respective isomers), a nonyl group (including respective isomers), a decyl group (including respective isomers), etc., preferably a methyl group, an ethyl group, a propyl group, an i-propyl group, a n-butyl group, an i-butyl group, a t-butyl group, a n-amyl group, an i-amyl group, a s-amyl group and a t-amyl group, more preferably a methyl group, an ethyl group, a propyl group, an i-propyl group, a n-butyl group, an i-butyl group and a t-butyl group.

As the $C_3$ to $C_{10}$ cycloalkyl group represented by R of the compound (I), there may be mentioned, for example, a $C_3$ to $C_{10}$ cycloalkyl group such as a cyclopropyl group, a cyclobutyl group, a cyclopentyl group, a cyclohexyl group, a cycloheptyl group, a cyclooctyl group, a cyclononyl group, a cyclodecyl group, etc., preferably a cyclopropyl group, a cyclobutyl group, a cyclopentyl group and a cyclohexyl group.

As the $C_7$ to $C_{10}$ aralkyl group represented by R of the compound (I), there may be mentioned, for example, a $C_3$ to $C_{10}$ aralkyl group such as a benzyl group, a phenethyl group, a 3-phenylpropyl group, a 4-phenylbutyl group, etc., preferably a benzyl group.

As such R, there may be preferably mentioned a hydrogen atom, a $C_1$ to $C_4$ alkyl group, a $C_3$ to $C_6$ cycloalkyl group and a benzyl group, more preferably a hydrogen atom and an ethyl group.

Among the compounds represented by the formula (I) having the above-mentioned R, as the 2,3,4-trifluoro-5-iodobenzoic acid and an ester thereof, there may be preferably mentioned 2,3,4-trifluoro-5-iodobenzoic acid, an alkyl ester having 1 to 5 carbon atoms such as
methyl 2,3,4-trifluoro-5-iodobenzoate,
ethyl 2,3,4-trifluoro-5-iodobenzoate,
n-propyl 2,3,4-trifluoro-5-iodobenzoate,
i-propyl 2,3,4-trifluoro-5-iodobenzoate,
n-butyl 2,3,4-trifluoro-5-iodobenzoate,
i-butyl 2,3,4-trifluoro-5-iodobenzoate,
s-butyl 2,3,4-trifluoro-5-iodobenzoate,
t-butyl 2,3,4-trifluoro-5-iodobenzoate,
n-amyl 2,3,4-trifluoro-5-iodobenzoate,
i-amyl 2,3,4-trifluoro-5-iodobenzoate,
s-amyl 2,3,4-trifluoro-5-iodobenzoate,
t-amyl 2,3,4-trifluoro-5-iodobenzoate, etc., a cycloalkyl ester having 3 to 6 carbon atoms such as
cyclopropyl 2,3,4-trifluoro-5-iodobenzoate,
cyclobutyl 2,3,4-trifluoro-5-iodobenzoate,
cyclopentyl 2,3,4-trifluoro-5-iodobenzoate,
cyclohexyl 2,3,4-trifluoro-5-iodobenzoate, etc.,
an aralkyl ester having 7 carbon atoms such as
benzyl 2,3,4-trifluoro-5-iodobenzoate, etc.,
more preferably
2,3,4-trifluoro-5-iodobenzoic acid, and
ethyl 2,3,4-trifluoro-5-iodobenzoate.

Also, among the compound represented by the formula (I) having the above-mentioned R, as the 2,3,4-trifluoro-5-trifluoromethylbenzoic acid and an ester thereof, there may be preferably mentioned:
2,3,4-trifluoro-5-trifluoromethylbenzoic acid,
an alkyl ester having 1 to 5 carbon atoms such as
methyl 2,3,4-trifluoro-5-trifluoromethylbenzoate,
ethyl 2,3,4-trifluoro-5-trifluoromethylbenzoate,
n-propyl 2,3,4-trifluoro-5-trifluoromethylbenzoate,
i-propyl 2,3,4-trifluoro-5-trifluoromethylbenzoate,
n-butyl 2,3,4-trifluoro-5-trifluoromethylbenzoate,
i-butyl 2,3,4-trifluoro-5-trifluoromethylbenzoate,
s-butyl 2,3,4-trifluoro-5-trifluoromethylbenzoate,
t-butyl 2,3,4-trifluoro-5-trifluoromethylbenzoate,
n-amyl 2,3,4-trifluoro-5-trifluoromethylbenzoate,
i-amyl 2,3,4-trifluoro-5-trifluoromethylbenzoate,
s-amyl 2,3,4-trifluoro-5-trifluoromethylbenzoate,
t-amyl 2,3,4-trifluoro-5-trifluoromethylbenzoate, etc.,
a cycloalkyl ester having 3 to 6 carbon atoms such as
cyclopropyl 2,3,4-trifluoro-5-trifluoromethylbenzoate,
cyclobutyl 2,3,4-trifluoro-5-trifluoromethylbenzoate,
cyclopentyl 2,3,4-trifluoro-5-trifluoromethylbenzoate,
cyclohexyl 2,3,4-trifluoro-5-trifluoromethylbenzoate, etc.,
an aralkyl ester having 7 carbon atoms such as
benzyl 2,3,4-trifluoro-5-trifluoromethylbenzoate, etc.,
more preferably
2,3,4-trifluoro-5-trifluoromethylbenzoic acid, and
ethyl 2,3,4-trifluoro-5-trifluoromethylbenzoate.

The preparation method of the trifluoro-trifluoromethylbenzoic acid esters of the present invention can be shown, for example, by the following

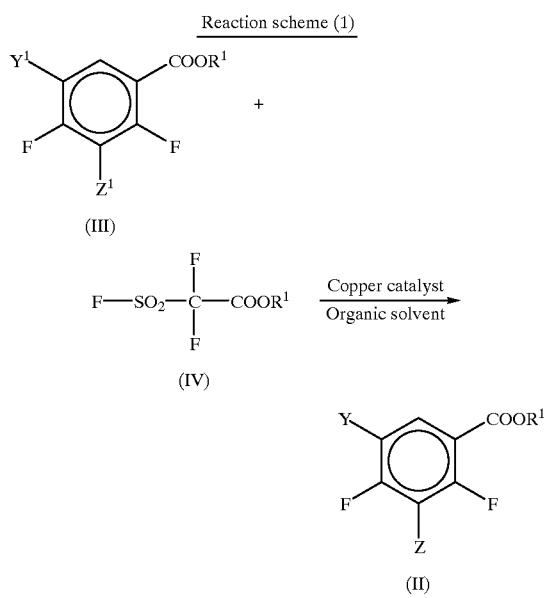

wherein $R^1$, Y, Z, $Y^1$ and $Z^1$ have the same meanings as defined above.

In the preparation method of the present invention, among the compound represented by the formula (III) to be used, $R^1$ of 2,3,4-trifluoro-5-iodobenzoic acid ester (hereinafter also referred to as Compound (IIIa)) and 2,4,5-trifluoro-3-iodobenzoic acid ester (hereinafter also referred to as Compound (IIIb)) represents a $C_1$ to $C_{10}$ alkyl group, a $C_3$ to $C_{10}$ cycloalkyl group or a $C_7$ to $C_{10}$ aralkyl group.

The $C_1$ to $C_{10}$ alkyl group shown by $R^1$ of Compound (III) has the same meaning as in the $C_1$ to $C_{10}$ alkyl group of the above-mentioned R.

The $C_3$ to $C_{10}$ cycloalkyl group shown by $R^1$ of Compound (III) has the same meaning as in the $C_3$ to $C_{10}$ cycloalkyl group of the above-mentioned R.

The $C_7$ to $C_{10}$ aralkyl group shown by $R^1$ of Compound (III) has the same meaning as in the $C_7$ to $C_{10}$ aralkyl group of the above-mentioned R.

Specific examples of the 2,3,4-trifluoro-5-iodobenzoic acid ester having such $R^1$ may include the above-mentioned 2,3,4-trifluoro-5-iodobenzoic acid esters.

Also, specific examples of the 2,4,5-trifluoro-3-iodobenzoic acid ester having such $R^1$ may be preferably mentioned
an alkyl ester having 1 to 5 carbon atoms of 2,4,5-trifluoro-3-iodobenzoic acid such as
methyl 2,4,5-trifluoro-3-iodobenzoate,
ethyl 2,4,5-trifluoro-3-iodobenzoate,
n-propyl 2,4,5-trifluoro-3-iodobenzoate,
i-propyl 2,4,5-trifluoro-3-iodobenzoate,
n-butyl 2,4,5-trifluoro-3-iodobenzoate,
i-butyl 2,4,5-trifluoro-3-iodobenzoate,
s-butyl 2,4,5-trifluoro-3-iodobenzoate,
t-butyl 2,4,5-trifluoro-3-iodobenzoate,
n-amyl 2,4,5-trifluoro-3-iodobenzoate,
i-amyl 2,4,5-trifluoro-3-iodobenzoate,
s-amyl 2,4,5-trifluoro-3-iodobenzoate,
t-amyl 2,4,5-trifluoro-3-iodobenzoate, etc.,
a cycloalkyl ester having 3 to 6 carbon atoms of 2,4,5-trifluoro-3-iodobenzoic acid such as
cyclopropyl 2,4,5-trifluoro-3-iodobenzoate,
cyclobutyl 2,4,5-trifluoro-3-iodobenzoate,
cyclopentyl 2,4,5-trifluoro-3-iodobenzoate,
cyclohexyl 2,4,5-trifluoro-3-iodobenzoate, etc., and
an aralkyl ester having 7 to 10 carbon atoms of 2,4,5-trifluoro-3-iodobenzoic acid such as
benzyl 2,4,5-trifluoro-3-iodobenzoate, etc.

$R^1$ in the 2,2-difluoro(fluorosulfonyl) acetic acid ester (in the following, it is also referred to as Compound (IV)) represented by the formula (IV) to be used in the process of the present invention shows the same meaning as in $R^1$ of the compound (III).

Specific examples of a 2,2-difluoro-(fluorosulfonyl)acetic acid ester represented by the formula (IV) having such a substitutent may include an alkyl ester having 1 to 5 carbon atoms of 2,2-difluoro-(fluorosulfonyl)acetic acid such as
methyl 2,2-difluoro-(fluorosulfonyl)acetate,
ethyl 2,2-difluoro-(fluorosulfonyl)acetate,
n-propyl 2,2-difluoro-(fluorosulfonyl)acetate,
i-propyl 2,2-difluoro-(fluorosulfonyl)acetate,
n-butyl 2,2-difluoro-(fluorosulfonyl)acetate,
i-butyl 2,2-difluoro-(fluorosulfonyl)acetate,
s-butyl 2,2-difluoro-(fluorosulfonyl)acetate,
t-butyl 2,2-difluoro-(fluorosulfonyl)acetate,
n-amyl 2,2-difluoro-(fluorosulfonyl)acetate,
i-amyl 2,2-difluoro-(fluorosulfonyl)acetate,
s-amyl 2,2-difluoro-(fluorosulfonyl)acetate,
t-amyl 2,2-difluoro-(fluorosulfonyl)acetate, etc.,
a cycloalkyl ester having 3 to 6 carbon atoms of 2,2-difluoro-(fluorosulfonyl)acetic acid such as cyclopropyl 2,2-difluoro-(fluorosulfonyl)acetate,
cyclobutyl 2,2-difluoro-(fluorosulfonyl)acetate,
cyclopentyl 2,2-difluoro-(fluorosulfonyl)acetate,
cyclohexyl 2,2-difluoro-(fluorosulfonyl)acetate, etc., and an aralkyl ester having 7 to 10 carbon atoms of 2,2-difluoro-(fluorosulfonyl)acetic acid such as
benzyl 2,2-difluoro-(fluorosulfonyl)acetate, etc.

The molar ratio of the compound (IV) to be used in the preparation process of the present invention is in the range of 1 to 5 moles, preferably in the range of 1 to 3 moles, more preferably in the range of 1.5 to 3.0 moles, further preferably in the range of 1.5 to 2.5 moles of the compound (IV) based on 1 mole of the compound (III).

As the organic solvent to be used in the preparation process of the present invention, it is not particularly limited so long as it does not participate in the reaction, but preferably an aprotic polar solvent, particularly an amide series solvent such as dimethylformamide, dimethylacetamide, N-methylpyrrolidone, N,N'-dimethylimidazolidone, etc., and a nitrile series solvent such as acetonitrile, benzonitrile, etc. are suitable, and particularly preferably dimethylformamide, dimethylacetamide.

An amount of the solvent to be used in the preparation process of the present invention can be used in the range wherein the weight concentration of Compound (III) being 1 to 50%, preferably in an amount which becomes in the range of 3 to 20%.

As the copper catalyst to be used in the preparation process of the present invention, there may be mentioned, for example, a monovalent copper halide, preferably cuprous chloride, cuprous bromide and cuprous iodide, and particularly preferably cuprous iodide.

The molar ratio of the copper catalyst to be used in the preparation process of the present invention can be employed in the range of 0.1 to 200 mole %, preferably in the range of 0.5 to 50 mole %, particularly preferably 1 to 10 mole % based on 1 mole of Compound (III).

The reaction temperature in the preparation process of the present invention is in the range of 0 to 200° C., preferably in the range of room temperature to 100° C.

The reaction time in the preparation process of the present invention largely depends on the reaction temperature, and is in the range of 0.5 to 20 hours.

The reaction pressure in the preparation process of the present invention is generally in a normal pressure, but the reaction may be carried out under reduced pressure or under pressure.

The reaction can be carried out in the same manner as in the usual organic reaction except that the reaction is carried out particularly in the absence of water. Isolation of the product from the reaction mixture is carried out by the method such as column purification, distillation, etc., similarly as in the usual reaction after the post-treatment, to obtain the desired compound (a 2,3,4-trifluoro-5-trifluoromethylbenzoic acid ester or a 2,4,5-trifluoro-3-trifluoromethylbenzoic acid ester) with a sufficiently high purity.

The resulting 2,3,4-trifluoro-5-trifluoromethylbenzoic acid ester or the 2,4,5-trifluoro-3-trifluoromethyl-benzoic acid ester can be converted into 2,3,4-trifluoro-5-trifluoromethylbenzoic acid or 2,4,5-trifluoro-3-trifluoromethylbenzoic acid with a good yield by subjecting to hydrolysis according to the usual method as shown in Example 4 or Reference example 4.

Next, the preparation process of the trifluoro-iodobenzoic acid ester of the present invention is explained.

The preparation process of the trifluoro-iodobenzoic acid of the present invention can be shown by, for example, the reaction scheme (2) as mentioned below:

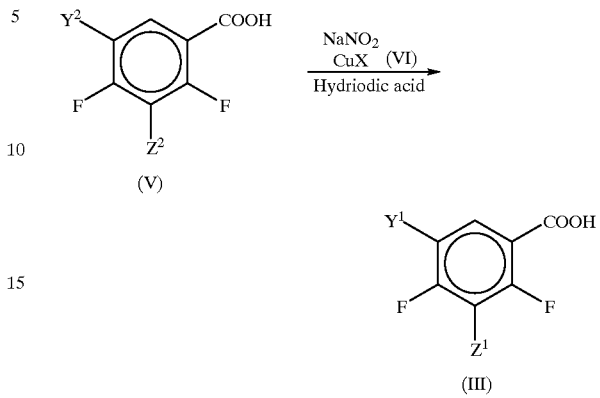

wherein X, $Y^1$, $Z^1$, $Y^2$ and $Z^2$ have the same meanings as defined above.

The molar ratio of hydriodic acid to be used in the preparation process of the present invention is generally in the range of 2.5 to 10 moles, preferably in the range of 4 to 7 moles based on one mole of the 5-amino-2,3,4-trifluorobenzoic acid or 3-amino-2,4,5-trifluorobenzoic acid represented by the formula (V).

X of the cuprous halide represented by the formula (VI) to be used in the preparation process of the present invention represents a halogen atom.

As the halogen atom shown by X in the cuprous halide, there maybe mentioned, for example, a fluorine atom, a chlorine atom, a bromine atom and an iodine atom, preferably a bromine atom and an iodine atom, more preferably an iodine atom.

The molar ratio of cuprous iodide to be used in the preparation process of the present invention is generally in the range of 0.05 to 2 moles, preferably in the range of 0.4 to 1.2 moles based on one mole of the 5-amino-2,3,4-trifluorobenzoic acid or 3-amino-2,4,5-trifluorobenzoic acid, but in this range (0.4 to 1.2 moles), there is no difference in the yield so that it is possible to decrease the amount to the stoichiometric amount or less.

As the reaction solvent to be used in the preparation process of the present invention, it is not particularly limited so long as it is not participate in the reaction, and it is preferably water, an alcoholic series solvent such as methanol, ethanol, etc., an aprotic polar solvent such as acetone, acetonitrile, dimethylformamide, etc. Also, amixed homogeneous solvent of water with an alcoholic series solvent, acetonitrile or acetone, etc. is also a good solvent.

An amount of the reaction solvent to be used in the present invention is generally within the range of 0.1 to 10 liters, preferably in the range of 0.1 to 3 liters based on one mole of the 5-amino-2,3,4-trifluorobenzoic acid or 3-amino-2,4,5-trifluorobenzoic acid.

As the alkali metal nitrite to be used in the preparation process of the present invention, there may be mentioned lithium nitrite, sodium nitrite, and potassium nitrite, preferably sodium nitrite and potassium nitrite, more preferably sodium nitrite.

The molar ratio of the alkali metal nitrite to be used in the present invention is in the range of 1 to 5 moles, preferably in the range of 1.5 to 3 moles based on one mole of the 5-amino-2,3,4-trifluorobenzoic acid or 3-amino-2,4,5-trifluorobenzoic acid The alkali metal nitrite may be added to the reaction system in a crystal form as such, or it is also possible to add the same in the form of a solution of water or of a mixed homogeneous solvent such as water with an alcoholic series solvent, acetonitrile, acetone, etc.

The reaction temperature in the preparation process of the present invention is:

1) until preparation of a mixed heterogeneous solution of 5-amino-2,3,4-trifluorobenzoic acid or 3-amino-2,4,5-trifluorobenzoic acid, an aqueous hydriodic acid solution and cuprous iodide, it is a neutralization reaction of the 5-amino-2,3,4-trifluorobenzoic acid or 3-amino-2,4,5-trifluorobenzoic acid with hydriodic acid. Therefore, there is no particular limitation, and the above-mentioned reaction can be carried out generally within the range of 0 to 100° C., but from operatability and to promote dissolution of 5-amino-2,3,4-trifluorobenzoic acid·hydriodide or 3-amino-2,4,5-trifluorobenzoic acid·hydriodide, it is preferably carried out generally under the state of heating to 100° C. or lower, and 2) the reaction temperatures at the time of adding the alkali metal nitrite at which the diazotization and iodization simultaneously occur, and thereafter are generally −5° C. to 50° C., preferably 0° C. to 30° C.

The reaction time in the preparation process of the present invention is 1) generally 0.25 to 1 hour until preparation of a mixed heterogeneous solution of 5-amino-2,3,4-trifluorobenzoic acid or 3-amino-2,4,5-trifluorobenzoic acid, an aqueous hydriodic acid solution and cuprous halide, and 2) after completion of addition of the alkali metal nitrite, it generally completes with 0.5 to 3 hours.

The reaction pressure in the preparation process of the present invention is generally carried out under atmospheric pressure since it accompanies occurrence of a nitrogen gas.

The 2,3,4-trifluoro-5-iodobenzoic acid or 3-amino-2,4,5-trifluorobenzoic acid which is a desired compound of the present invention can be isolated according to the method wherein 1) a method of setting the pH of the reaction mixture to 4 or less by a mineral acid such as hydrochloric acid, a sulfuric acid, a phosphoric acid, etc., adding a water-immiscible organic solvent such as toluene, ethyl acetate, diethyl ether, etc., and after dehydrating the organic layer, it is concentrated, dried and isolated, or 2) a method of setting the pH of the reaction mixture to 4 to 8 by using an inorganic base such as sodium hydroxide, sodium hydrogen carbonate, potassium hydrogen carbonate, an aqueous ammonia, etc., or an organic base such as triethylamine, diethylamine, etc., and after removing insoluble materials by filtration, adding a mineral acid such as hydrochloric acid, sulfuric acid, phosphoric acid, etc. to the filtrate to lower the pH thereof 3 or less, preferably the pH of 2.5 or less whereby crystallizing and isolating the product, or the like.

Utilizability in Industry

The 2,3,4-trifluoro-5-trifluoromethylbenzoic acid and an ester thereof which are the compounds of the present invention are useful as a starting material for synthesizing a quinolone carboxylic acid series compound which is useful as a medicine, particularly as an antibacterial agent or an antiviral agent. Also, by allowing the 2,3,4-trifluoro-5-iodobenzoic acid ester or the 2,4,5-trifluoro-3-iodobenzoic acid ester to react with the 2,2-difluoro-(fluorosulfonyl)-acetic acid ester in the presence of a copper catalyst in an organic solvent, the desired compounds, 2,3,4-trifluoro-5-trifluoromethylbenzoic acid esters or the 2,4,5-trifluoro-3-trifluoromethylbenzoic acid esters can be obtained with a good yield without danger of an explosion. The 2,3,4-trifluoro-5-trifluoromethylbenzoic acid esters or the 2,4,5-trifluoro-3-trifluoromethylbenzoic acid esters can be easily converted into 2,3,4-trifluoro-5-trifluoromethylbenzoic acid or 2,4,5-trifluoro-3-trifluoromethylbenzoic acid.

Also, the 2,3,4-trifluoro-5-iodobenzoic acid which is the compound of the present invention is useful as a starting material for producing 2,3,4-trifluoro-5-trifluoromethylbenzoic acid which is an important intermediate for synthesizing a quinolone carboxylic acid series compound which is useful as a medicine, particularly an antibacterial agent or an antiviral agent. By reacting 5-amino-2,3,4-trifluorobenzoic acid with the alkali metal nitrite in the presence of hydriodic acid and the cuprous halide represented by the formula (VI), 2,3,4-trifluoro-5-iodobenzoic acid which is the desired compound can be obtained with a good yield.

According to the present invention, by reacting 3-amino-2,4,5-trifluorobenzoic acid with the alkali metal nitrite in the presence of hydriodic acid and the cuprous halide represented by the formula (VI), 2,4,5-trifluoro-3-iodobenzoic acid which is the desired compound can be obtained with a good yield.

EXAMPLES

In the following, the present invention is explained in more detail by referring to Examples, but the scope of the present invention is not limited to them. Analytical conditions of a high performance liquid chromatography (hereinafter abbreviated to as HPLC) in Examples and Reference examples are as follows.

Analytical conditions of HPLC

Column; TSK-gel Super ODS (trade name: available from Toso Kabushiki Kaisha), 4.6 mmφ×100 mm Eluent; Acetonitrile:water=2:3 (V/V), IPC-TBACl=1.34 g/l Temperature; 40° C.

Flow rate; 1 ml/min

Detection wavelength; 275 nm

Internal standard substance; 1-Phenyl-1-butanone

Reference Example 1

A mixed solution of 10.56 g (60 mmol) of 2,3,4-trifluorobenzoic acid and 15.6 ml of sulfuric acid was ice-cooled, and 11.4 ml of a fumed nitric acid was added dropwise thereto at 5 to 30° C. and the mixture was stirred at the same temperature for 5 hours to complete the reaction.

After completion of the reaction, the resulting reaction mixture was added to 400 ml of ice-water, and then, extracted twice with 150 ml of ethyl acetate. The combined organic layers were washed with 100 ml of water, dried over anhydrous magnesium sulfate, and then, filtered and evaporated to dryness. The resulting product obtained by evaporation to dryness was added to 50 ml of water and the mixture was stirred to wash the product. After collecting the precipitates by filtration, the precipitates were dried under reduced pressure to obtain 10.0 g (45.2 mmol) of 2,3,4-trifluoro-5-nitrobenzoic acid.

Melting point: 134–135° C.

$^1$H-NMR (DMSO, 400 MHz)

δ (ppm)=8.68 (H, ddd, Ar-H)

Reference Example 2

A mixed solution was obtained by mixing 9.0 g (40.7 mmol) of 2,3,4-trifluoro-5-nitrobenzoic acid obtained in Reference example 1, 100 ml of ethanol and 1.0 g of 20% Pd/C (50% hydrated material) under nitrogen atmosphere. A hydrogen gas was passed through the resulting mixed solution at room temperature to carry out the reaction.

After completion of the reaction, the resulting reaction solution was filtered and the filtrate was evaporated to dryness. The residue was recrystallized from hexane-ethyl acetate. The resulting crystals were collected by filtration and dried under reduced pressure to obtain 7.09 g (37.1 mmol) of 5-amino-2,3,4-trifluorobenzoic acid.

Melting point: 164.5–166° C.

$^1$H-NMR (DMSO, 400 MHz)

$\delta$ (ppm) = 5.57 (2H, br, NH$_2$)

7.09 (H, ddd, Ar—H)

13.29 (H, br, COOH)

Example 1

A mixed solution was obtained by mixing 3.3 g (17.3 mmol) of 5-amino-2,3,4-trifluorobenzoic acid, 11.1 g (51.8 mmol) of a 57% aqueous hydriodic acid solution, 3.3 ml of water and 1.64 g (8.65 mmol) of cuprous iodide. While cooling the resulting mixed solution to maintain the inner temperature to 15 to 30°C., an aqueous solution of 1.19 g (17.2 mmol) of sodium nitrite and 2.4 ml of water was added dropwise thereto. After completion of the dropwise addition, the mixture was stirred for 30 minutes until gas evolution was ceased.

After gas evolution being ceased, to the resulting reaction mixture (1) was further added 11.1 g (51.8 mmol) of a 57% aqueous hydriodic acid solution, and then, an aqueous solution of 1.19 g (17.2 mmol) of sodium nitrite and 2.4 ml of water was added thereto dropwise. After completion of the dropwise addition, the mixture was stirred for 30 minutes until gas evolution was ceased. This operation was repeated three times in total.

After completion of the reaction, to the resulting reaction mixture (2) was added 9 g (71 mmol) of sodium hydrogen sulfite, and then, the pH of the reaction mixture was made 2.5 with a 6N aqueous sodium hydroxide solution and the reaction mixture was extracted with 40 ml of toluene. The organic layer was dried over anhydrous magnesium sulfate, filtered, and then, evaporated to dryness to obtain 4.45 g of 2,3,4-trifluoro-5-iodobenzoic acid as crystals.

Melting point: 167–171° C.

$^1$H-NMR (CDCl$_3$, 400 MHz)

$\delta$ (ppm) = 8.06 (H, ddd, Ar—H)

13.82 (H, br, COOH)

Example 2

A mixed solution of 4.45 g (14.7 mmol) of 2,3,4-trifluoro-5-iodobenzoic acid obtained in Example 1, 18 ml of ethanol, 18 ml of toluene and 1.73 g of conc. sulfuric acid was reacted under reflux for 8 hours. During the reaction, while adding 35 ml of ethanol, 30 ml of the solvent was removed by distillation under normal pressure.

After completion of the reaction, the resulting reaction mixture was cooled to room temperature, and then, the reaction mixture was concentrated. To the concentrate was added 30 ml of toluene, and the mixture was washed twice with 20 ml of water. The organic layer was dried over anhydrous magnesium sulfate, filtered and concentrated under reduced pressure to obtain 6.02 g of the concentrate. The concentrate was purified by silica gel column chromatography (eluent; hexane:ethyl acetate=20:1) to obtain 3.91 g (11.8 mmol) of ethyl 2,3,4-trifluoro-5-iodobenzoate.

Melting point: 33–34° C.

$^1$H-NMR (CDCl$_3$, 400 MHz)

$\delta$ (ppm) = 1.41 (3H, t, CH$_3$)

4.41 (2H, q, O—CH$_2$—)

8.14 (H, ddd, Ar—H)

Example 3

To a mixture of 229 mg (1.18 mmol) of cuprous iodide and 26 ml of dimethylformamide were added 6.8 g (35.4 mmol) of methyl 2,2-difluoro-(fluorosulfonyl)acetate and 3.9 g (11.8 mmol) of ethyl 2,3,4-trifluoro-5-iodobenzoate, and the mixture was heated and stirred at 85 to 94° C. for 9 hours whereby the reagents were reacted.

After completion of the reaction, the resulting reaction mixture was added dropwise to a mixture of 40 ml of hexane and 30 ml of a saturated aqueous sodium hydrogen carbonate solution. The hexane layer was separated and the aqueous layer was extracted with 20 ml of hexane. The combined hexane layers were dried over anhydrous magnesium sulfate. The hexane layer was filtered and concentrated, and the concentrate was distilled under reduced pressure to obtain 2.87 g (10.5 mmol) of the desired ethyl 2,3,4-trifluoro-5-trifluoromethylbenzoate.

Boiling point: 77 to 79° C./6 mmHg.

$^1$H-NMR (CDCl$_3$, 400 MHz)

$\delta$ (ppm) = 1.41 (3H, t, CH$_3$)

4.44 (2H, q, O—CH$_2$—)

8.05 (H, ddd, Ar—H)

Example 4

A mixture of 2.5 g (9.2 mmol) of ethyl 2,3,4-trifluoro-5-trifluoromethylbenzoate obtained in Example 3, 7.45 ml of formic acid, 1.51 ml of water and 3.5 g of p-toluenesulfonic acid monohydrate was refluxed and stirred for 6 hours. During the reaction, 2 ml of the solvent was removed by distillation from the reaction system, and a mixed solution of 2 ml of formic acid and 0.4 ml of water was added to the reaction system.

After completion of the reaction, the resulting reaction mixture was cooled, and then, 18 ml of water and 18 ml of methylene chloride were added thereto The methylene chloride layer was collected by separation, and the aqueous layer was further extracted twice with 20 ml of methylene chloride. The combined methylene chloride layers were dried over anhydrous magnesium sulfate, filtered and concentrated to obtain 2.18 g of the concentrated residue. To the concentrated residue was added 25 ml of hexane and the mixture was heated. The resulting homogeneous solution was cooled to 0 to 5° C. to precipitate crystals. The resulting crystals were collected by filtration, washed with hexane and air-dried to obtain 1.42 g (5.82 mmol) of 2,3,4-trifluoro-5-trifluoromethylbenzoic acid.

Melting point: 82 to 84° C.

¹H-NMR (CDCl₃, 400 MHz)

δ (ppm) = 8.16 (H, ddd, Ar—H)

9.49 (H, br, COOH)

Example 5

In a flask with a 10 liter volume were charged 191 g (1.00 mol) of 3-amino-2,4,5-trifluorobenzoic acid, 1.01 kg (4.5 mol) of a 57% aqueous hydriodic acid solution and 1.9 liters of water, and the mixture was heated to 50° C. to make a homogeneous solution and then, cooled to 20° C. After adding 95.2 g (0.50 mol) of cuprous iodide, 759 ml of an aqueous solution containing 152 g (2.2 mol) of sodium nitrite was added dropwise to the mixture over 2 hours while cooling it to maintain the inner temperature to 20 to 25° C. After completion of the dropwise addition, stirring was further continued for one hour to carry out the reaction.

After completion of the reaction, 316 g (2.0 mol) of sodium thiosulfate and 20 ml of conc. hydrochloric acid were added to the resulting reaction mixture to make the pH thereof 1.56, and then, the reaction mixture was extracted with toluene (860 ml×three times). The organic layer was dried over anhydrous magnesium sulfate, filtered and then, concentrated to obtain crystals of 2,4,5-trifluoro-3-iodobenzoic acid (280 g, purity: about 96%, Yield based on 3-amino-2,4,5-trifluorobenzoic acid: 89%). Melting point 122 to 124° C.

Examples 6 to 8

The amount to be used of 3-amino-2,4,5-trifluorobenzoic acid in Example 5 was made 5.0 g (26 mmol), and changing molar ratios of the 57% hydriodic acid, and sodium nitrite based on the 3-amino-2,4,5-trifluorobenzoic acid, a kind of the solvent and a reaction temperature of addition of sodium nitrite, the reaction was carried out. The results are shown in the following Table 1. As for the amounts of reagents not mentioned in Table 1, these were decreased depending on decrease in an amount of the 3-amino-2,4,5-trifluorobenzoic acid to be used.

After completion of the reaction, the reaction mixture was cooled to room temperature, then 12.5 ml of a saturated aqueous sodium chloride solution was added to the reaction mixture and the organic layer was separated. The aqueous layer was further extracted with 12 ml of toluene. The combined organic layers were washed with 12.5 ml of a saturated sodium hydrogen carbonate aqueous solution, and then, dried over anhydrous magnesium sulfate. After filtration, concentration of the mixture was carried out to obtain 4.32 g of ethyl 2,4,5-trifluoro-3-iodobenzoate (pure content: 4.05 g, 12.3 mmol, Yield based on 2,4,5-trifluoro-3-iodobenzoic acid: 98%).

Example 9

To a mixture of 311.3 mg (1.65 mmol) of cuprous iodide and 72 ml of dimethylformamide were added 12.56 g (66 mmol) of methyl 2,2-difluoro-(fluorosulfonyl)acetate and 11.30 g (purity: 93%, 33 mmol) of ethyl 2,4,5-trifluoro-3-iodobenzoate, and the mixture was heated to 80 to 85° C. for 7 hours.

After completion of the reaction, the resulting reaction mixture was added dropwise to a mixture of 83 ml of hexane and 83 ml of a saturated aqueous sodium hydrogen carbonate solution. The hexane layer was collected by separation and dried over anhydrous magnesium sulfate. In 9.23 g of the residue obtained by concentrating the hexane under reduced pressure, it was found by the HPLC analysis that 7.23 g (24.4 mmol) of ethyl 2,4,5-trifluoro-3-trifluoromethylbenzoate which is the desired compound had been contained.

Example 10

2860 ml of dimethylformamide were added 500 g (2.6 mol) of methyl 2,2-difluoro-(fluorosulfonyl) acetate and 441.4 g (purity: 97.3%, 1.3 mol) of ethyl 2,4,5-trifluoro-3-iodobenzoate, and the mixture was heated to 80 to 86° C. and stirred for 7 hours to react the reactants.

After completion of the reaction, the resulting reaction mixture was added dropwise to a mixture of 3250 ml of hexane and 3250 ml of a saturated aqueous sodium hydrogen carbonate solution. After filtration, the hexane layer was collected by separation and dried over anhydrous magnesium sulfate. In 642 g of the residue obtained by concentrating the hexane solution under reduced pressure, it was found that 278.4 g (1.02 mol) of the desired product, ethyl 2,4,5-trifluoro-3-trifluoromethylbenzoate had been contained by the gas chromatography analysis. Incidentally, the same results can be obtained by the HPLC analysis.

TABLE 1

| Example | Amount of NaNO₂ to be used | Amount of 57% hydriodic to be used | Reaction temperature when NaNO₂ is added | Kind of reaction solvent | Yield (%) |
|---|---|---|---|---|---|
| 6 | 182 mmol | 91 mmol | 0 to 5° C. | Water | 88 |
| 7 | 182 mmol | 104 mmol | 20 to 25° C. | Water: Acetone = 4:1 | 89 |
| 8 | 65 mmol | 52 mmol | 20 to 25° C. | Water | 66 |

Reference Example 3

A mixed solution of 4.0 g (purity: 94.4%, pure content: 3.78 g, 12.5 mmol) of 2,4,5-trifluoro-3-iodobenzoic acid, 12.5 ml of ethanol, 12.5 ml of toluene and 1.35 ml (25 mmol) of conc. sulfuric acid was reacted under reflux for 3 hours. Thereafter, while adding a mixed solvent of ethanol:toluene=3:2 in an amount equal to the distilled amount, 75 ml of the solvent was removed by distillation under normal pressure.

The same operation was repeated twice, and the combined concentrates were distilled under reduced pressure by attaching a 30 cm Widmer fractionating column rectification apparatus. Fractions boiling at 74 to 79° C./0.39 kPa were collected. Collected amount of ethyl 2,4,5-trifluoro-3-trifluoromethylbenzoate: 567 g, Purity: 92.2%, 1.927 mol, Obtained yield based on ethyl 2,4,5-trifluoro-3-iodobenzoate: 74.1%.

Analytical conditions of Gas chromatography

Column: PEG-20M (trade name, available from GL Science Kabushiki Kaisha)

Carrier: 10% Uniport HP (trade name, available from GL Science Kabushiki Kaisha), 60/80 mesh, 3.5 mmϕ×2 m Column temperature: 100→200° C. (7.5° C./min.)

Injection temperature; 220° C.

Carrier gas: Nitrogen

Detector temperature; 220° C. (FID)

Example 11

To a mixture of 0.095 g (0.5 mmol) of cuprous iodide and 22 ml of dimethylacetamide were added 3.84 g (20 mmol) of methyl 2,2-difluoro-(fluorosulfonyl)acetate and 3.4 g (purity 97.3%, 10 mmol) of ethyl 2,4,5-trifluoro-3-iodobenzoate, and the mixture was heated to 86 to 90° C. and stirred for 7.5 hours to react the reactants.

After completion of the reaction, the resulting reaction mixture was added dropwise to a mixture of 25 ml of hexane and 25 ml of a saturated aqueous sodium hydrogen carbonate solution. After filtration, the hexane layer was collected by separation and dried over anhydrous magnesium sulfate. When the hexane solution was analyzed by HPLC, it was found that 2.04 g (7.5 mmol, Yield based on ethyl 2,4,5-trifluoro-3-iodobenzoate: 75%) of the desired product ethyl 2,4,5-trifluoro-3-trifluoromethylbenzoate had been contained therein.

Reference Example 4

A mixture of 567 g (purity: 92.2%, 1.927 mol) of ethyl 2,4,5-trifluoro-3-trifluoromethylbenzoate obtained in the above-mentioned Example 10, 1580 ml of acetic acid, 316 ml of water and 733 g of p-toluenesulfonic acid monohydrate was refluxed for 8 hours with stirring. 250 ml of the solvent was distilled off from the reaction mixture and a mixture of 280 ml of acetic acid and 42 ml of water was added to the reaction mixture. These operation were performed twice respectively during the reaction.

After completion of the reaction, 1930 ml of water was added to the resulting reaction mixture to cool the mixture, and 3.85 liters of toluene were added thereto. The solutions were separated, and the aqueous layer was further extracted with 1.93 liters of toluene three times. The combined toluene layers were dried over anhydrous magnesium sulfate, filtered and concentrated, and then, 1.9 liters of hexane were added to the concentrated residue and the mixture was heated. The resulting homogeneous solution was cooled to 0 to −6.5° C. and crystals were precipitated. The resulting crystals were collected by filtration, washed with hexane, and air-dried to obtain 401 g (1.64 mol, purity: 99.8%) of 2,4,5-trifluoro-3-trifluoromethylbenzoic acid.

What is claimed is:

1. A process for producing trifluoro-iodobenzoic acid represented by the formula (III'):

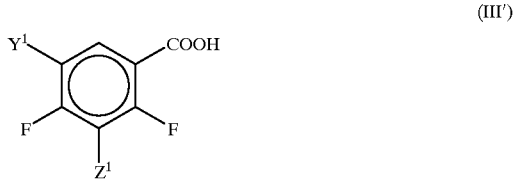

(III')

wherein $Y^1$ represents a fluorine atom or an iodine atom; and $Z^1$ represents an iodine atom when $Y^1$ is a fluorine atom, or a fluorine atom when $Y^1$ is an iodine atom, which comprises allowing an amino-trifluorobenzoic acid represented by the formula (V):

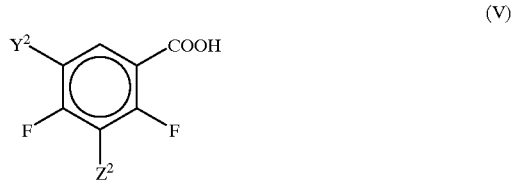

(V)

wherein $Y^2$ represents an amino group or a fluorine atom; $Z^2$ represents a fluorine atom when $Y^2$ is an amino group, or an amino group when $Y^2$ is a fluorine atom, to react with hydriodic acid in the presence of an alkali metal nitrite and a cuprous halide represented by the formula (VI):

CuX       (VI)

wherein X represents a halogen atom, in a solvent.

2. The preparation process according to claim 1, wherein the alkali metal nitrite is added to a mixed heterogeneous solution of 3-amino-2,4,5-trifluorobenzoic acid, hydriodic acid and cuprous halide.

3. The preparation process according to claim 1, wherein the alkali metal nitrite is added to a mixed heterogeneous solution of 5-amino-2,3,4-trifluorobenzoic acid, hydriodic acid and cuprous halide.

4. The preparation process according to claim 1, wherein the cuprous halide is cuprous iodide.

5. The preparation process according to claim 1, wherein the amount of cuprous halide to be used is a stoichiometric amount or less based on that of the amino-trifluorobenzoic acid.

6. The preparation process according to claim 1, wherein the amount of hydriodic acid to be used is 2.5 to 10 moles per mole of the amino-trifluorobenzoic acid.

7. The preparation process according to claim 1, wherein the alkali metal nitrite is sodium nitrite or potassium nitrite.

* * * * *